United States Patent [19]
Govind et al.

[11] Patent Number: 6,039,932
[45] Date of Patent: Mar. 21, 2000

[54] MEDICINAL INHALATION AEROSOL FORMULATIONS CONTAINING BUDESONIDE

[75] Inventors: Nayna Govind, West Bridgford; Philip A. Jinks, Mountsorrel, both of United Kingdom; Danna L. Ross, Pine Springs, Minn.; Gary H. Ward, San Diego, Calif.

[73] Assignee: 3M Innovative Properties Company, St. Paul, Minn.

[21] Appl. No.: 08/937,520

[22] Filed: Sep. 25, 1997

Related U.S. Application Data

[60] Provisional application No. 60/032,092, Dec. 3, 1996.

[30] Foreign Application Priority Data

Sep. 27, 1996 [GB] United Kingdom .................. 9620187

[51] Int. Cl.$^7$ ....................................................... A61K 9/12
[52] U.S. Cl. .............................................. 424/45; 424/46
[58] Field of Search ........................................ 424/45, 46

[56] References Cited

U.S. PATENT DOCUMENTS

| | | |
|---|---|---|
| 5,225,183 | 7/1993 | Purewal et al. ............................ 424/45 |
| 5,345,980 | 9/1994 | Burt et al. ..................................... 141/3 |
| 5,415,853 | 5/1995 | Hettche et al. ............................ 424/45 |
| 5,439,670 | 8/1995 | Purewal et al. ............................ 424/45 |
| 5,492,688 | 2/1996 | Byron et al. ................................ 424/45 |
| 5,605,674 | 2/1997 | Purewal et al. ............................ 424/45 |
| 5,658,549 | 8/1997 | Akehurst et al. .......................... 424/45 |
| 5,674,473 | 10/1997 | Purewal et al. ............................ 424/45 |
| 5,681,545 | 10/1997 | Purewal et al. ............................ 424/45 |
| 5,683,677 | 11/1997 | Purewal et al. ............................ 424/45 |
| 5,695,743 | 12/1997 | Purewal et al. ............................ 424/45 |
| 5,720,940 | 2/1998 | Purewal et al. ............................ 424/45 |
| 5,736,124 | 4/1998 | Akehurst et al. .......................... 424/45 |

FOREIGN PATENT DOCUMENTS

| | | |
|---|---|---|
| 372777 | 6/1990 | European Pat. Off. . |
| 384371 | 8/1990 | European Pat. Off. . |
| 504112 | 9/1992 | European Pat. Off. . |
| 518600 | 12/1992 | European Pat. Off. . |
| 518601 | 12/1992 | European Pat. Off. . |
| 0533731 | 3/1993 | European Pat. Off. . |
| 534731 | 3/1993 | European Pat. Off. . |
| 550031 | 7/1993 | European Pat. Off. . |
| 605578 | 7/1994 | European Pat. Off. . |
| 617610 | 10/1994 | European Pat. Off. . |
| 0633019 | 1/1995 | European Pat. Off. . |
| 653205 | 5/1995 | European Pat. Off. . |
| 91/04011 | 4/1991 | WIPO . |
| 91/11495 | 8/1991 | WIPO . |
| 91/11496 | 8/1991 | WIPO . |
| 92/22287 | 12/1992 | WIPO . |
| 93/11745 | 6/1993 | WIPO . |
| 93/11747 | 6/1993 | WIPO . |
| 93/18746 | 9/1993 | WIPO . |
| 94/21228 | 9/1994 | WIPO . |
| 94/21229 | 9/1994 | WIPO . |
| 9508603 | 3/1995 | WIPO . |
| 95/15151 | 6/1995 | WIPO . |
| 9527476 | 10/1995 | WIPO . |
| 96/09816 | 4/1996 | WIPO . |
| 96/09831 | 4/1996 | WIPO . |
| 96/18384 | 6/1996 | WIPO . |
| 9619198 | 6/1996 | WIPO . |

*Primary Examiner*—Raj Bawa
*Attorney, Agent, or Firm*—Ted K. Ringsred; MarySusan Howard; Robert W. Sprague

[57] ABSTRACT

A pharmaceutical aerosol formulation, suitable for administration by oral or nasal inhalation, containing a suspension of particulate budesonide, hydrofluoroalkane propellant and, optionally, additional hydrofluoroalkane propellants, surfactant selected from oleic acid, sorbitan oleates and lecithin, and adjuvant have a Kauri-butanol value of at least 10.

15 Claims, No Drawings

MEDICINAL INHALATION AEROSOL FORMULATIONS CONTAINING BUDESONIDE

This application claims priority under 35 USC 119 to U.S. provisional application 60/032,092, filed Dec. 3, 1996, and to Great Britain application GB 9620187.6, filed Sep. 27, 1996.

BACKGROUND

This invention relates to medicinal aerosol formulations and in particular to aerosol formulations containing budesoride which are suitable for administration to the respiratory system of a patient.

Pharmaceutical suspension aerosol formulations are known which use a mixture of liquid chlorofluorocarbons as the propellant. Fluorotrichloromethane, dichlorodifluoromethane and dichlorotetrafluoroethane are the most commonly used propellants in aerosol formulations for administration by inhalation.

Chlorofluorocarbons (CFCs), however, have been implicated in the destruction of the ozone layer and their production is being phased out. Hydrofluoroalkanes, such as hydrofluoroalkane 134a (HFA 134a, 1,1,1,2-tetrafluoroethane) and hydrofluoroalkane 227 (HFA 227, 1,1,1,2,3,3,3-heptafluoropropane), are viewed as being, more ozone friendly than many chlorofluorocarbon propellants; furthermrore, they have low toxicity and vapor pressures suitable for use in aerosols.

W091/04011, W091/11495, W091/1496, W093/11745, W093/11747, W094/21228, W095/15151, W096/9816, W096/9831, EP-A-0372777, EP-A-0384371, EP-A-0518600, EP-A-0518601, EP-A-0550031, EP-A-0587790 and U.S. Pat. No. 5,492,688 disclose aerosol formulations in which the propellant comprises a hydrofluoroalkane.

EP-A-0605578 discloses pharmaceutical aerosol compositions comprising a liquefied hydrofluoralkane, a powdered medicament and a polymer, soluble in the hydrofluoroalkane, having recurring structural units selected from amide containing units and carboxylic acid ester containing units. One formulation consists of HFA 227, budesonide and a polyvinylpyrrolidone/vinyl acetate copolymer and a further formulation additionally comprises polyethylene glycol.

W093/18746 discloses a pharmaceutical aerosol formulation consisting of HFA 227, budesonide, 1% by weight pol,yoxyethylene-25-glyceryl-trioleate and 1% by weight ethanol.

EP-A-0504112 discloses inter alia a formulation comprising 0.312% budesonide, 0.039% Myvacet 9-45, 1.171% Tween 60, 11.50% ethanol and 86.978% HFA 227. The ethanol content of this formulation is sufficient to dissolve a substantial proportion of the budesonide and is likely to exhibit crystal growth of budesonide particles.

W094/21229 discloses formulations comprising 0.03% particulate budesonide, 0.05% dispersing aid and 99.92% propellant which was either HFA 134a or HFA 227. The dispersing aids are derived from acetyl-oligo-L-lactic acids. The ingredients were homogenized using ultrasound. After storage, each formulation was shaken by hand then observed on standing. Each of the suspensions is said to flocculate within 5 seconds after shaking ceased.

Suspension formulations of budesonide have a propensity to rapidly form coarse flocs upon dispersion and redispersion which may deleteriously affect dosage reproducibility. There is also a tendency for budesonide to deposit from suspension onto the walls of the container.

The teaching of the state of the art does not provide a ready solution to these problems.

SUMMARY

According to one aspect of the present invention there is provided a pharmaceutical aerosol formulation suitable for administration to a patient by oral or nasal inhalation consisting of a suspension of particulate budesonide, a hydrofluoroalkane propellant and optionally one or more of:
  (i) one or more additional hydrofluoroalkane propellants
  (ii) surfactant selected from oleic acid, sorbitan oleates and lecithin, and
  (iii) adjuvant having a Kauri-butanol value of at least 10.

It has been found that it is possible to achieve stable suspensions of particulate budesonide by employing up to 3% of an adjuvant having a Kauri-butanol value greater than 10, e.g., ethanol. In such formulations, the level of adjuvant is selected to decrease the propensity for rapid formation of coarse flocs and for deposition of drug on manufacturing equipment and on the internal surfaces of the container closure system of the inhaler. However, the levels are not so high as to cause significant solubilization of drug, leading to problems of chemical degradation and particle size increase on storage.

According to a further aspect of the present invention there is provided a pharmaceutical aerosol formulation suitable for administration to a patient by oral or nasal inhalation consisting essentially of a suspension of budesonide particles in a mixture of hydrofluoroalkane propellants and optionally one or more excipients selected from:
  (i) an adjuvant having a Kauri-butanol value of at least 10,
  (ii) the combination of an adjuvant (i) and a surfactant selected from oleic acid, sorbitan oleates and lecithin, and
such that the liquid mixture has a density at 20° C. substantially equal to the density of budesonide.

It has been found that it is possible to achieve stable suspensions of particulate budesonide by employing a mixture of HFA propellants by matching the density of the propellant mixture to be substantially identical to the density of budesonide. Such formulations are referred to herein as "density matched". The particles preferably have an average size in the range 1 to 10 $\mu$m.

In addition to its use for the control of asthma, budesonide is particularly suited for nasal delivery in the treatment cf allergic rhinitis. Formulations for this application preferably do not contain high levels of ethanol in order to avoid irritation of the nasal mucosa. Levels of about 1% by weight ethanol have been found not to produce irritation.

Formulations of the invention exhibit substantially no growth in particle size or change in crystal morphology of the drug over a prolonged period, are substantially and readily redispersible, and upon redispersion do not flocculate so quickly as to prevent reproducible dosing of the drug.

It has been found that budesonide particles will sink when suspended in 100% HFA 134a but float when suspended in 100% HFA 227.

It has been found that it is possible to match the density of budesonide using a propellant mixture of HFA's, particularly a mixture of HFA 134a and HFA 227. Suitable propellant mixtures comprise from 15 to 35%, HFA 227 and correspondingly 65 to 85% by weight HFA 134a.

Although density matched mixtures of HFA propellants provide improved formulations of suspended budesonide compared with the use of single propellants, such mixtures do not necessarily prevent the formation of large flocs or prevent drug deposition on the walls of the container or equipment used in preparing the formulation. It has been found that the presence of an adjuvant having a Kauri-butanol value of at least 10 may improve the properties of both density matched and other formulations of suspended budesonide. The preferred adjuvant is ethanol, but other adjuvants such as isopropyl alcohol and polyethylene glycol may be used. The adjuvant is preferably present in a proportion which does not lead to excessive crystal growth or produce irritation wheei inhaled, particularly when inhaled intranasally.

In addition, small amounts of surfactant, preferably from 0.0005 to 0.01% may provide improved properties, e.g., preventing particles adhering to surfaces and providing lubrication for valve components in contact with the formulation. The surfactant is selected from oleic acid, lecithin and sorbitan oleates, e.g., sorbitan monooleate, sorbitan sesquioleate and scrbitan trioleate. The preferred surfactant is oleic acid.

The budesonide is generally present to provide a dose of from 1 to 8 mg/ml of formulation. Exemplary doses are 1, 2, 4, and 8 mg/ml. Such doses are achieved using a concentration of budesonide of :from about 0.075 to 0.66% by weight of the formulation depending upon the precise formulation.

Preferred formulations in accordance with the invention consist of:

particulate budesonide
oleic acid
ethanol
HFA 134a
HFA 227

It is conventional practice when preparing aerosol formulations to mix the drug with the highest boiling point material and thereafter mix with the propellant. However, when making the formulation; of the present invention it is important to ensure the budesonide does not come into contact with high concentrations, e.g., above 5% w/w, of ethanol since the drug would dissolve leading to instability and crystal growth problems in the final formulation. Preferably the maximum concentration of ethanol during formulation is less than 1%.

When preparing formulations of the invention with a content of up to 1% w/w ethanol, the concentration of ethanol at any stage in the presence of budesonide must be maintained no higher than this level. A procedure for preparing a budesonide suspension formulation by cold-filling is as follows:

a) Add all of the formulation quantity of HFA 134a and half of the formulation quantity of HFA 227 to a batching vessel.
b) Prepare a first concentrate containing any surfactant and at least 85% of the formulation quantity of ethanol. Add this to the batching vessel.
c) Prepare a second concentrate containing the other half of the formulation quantity of HFA 227 and the remainder of the ethanol (i.e., no more than 1% w/w of the second concentrate), and add the micronized drug while mixing under high shear. Add the second concentrate to the batching vessel.

DETAILED DESCRIPTION

The invention will now be described with reference to the following Examples which employed micronized budesonide.

EXAMPLES 1 to 9

Formulations were prepared using HFA 134a as propellant. Particulate budesonide was present at 0.33% by weight optionally with ethanol and surfactant as reported in the following table.

| | | Surfactant | |
|---|---|---|---|
| Example | % Ethanol | % Oleic Acid | % Span 85 |
| 1 | 0 | 0 | 0 |
| 2 | 1 | 0 | 0 |
| 3 | 1 | 0.01 | 0 |
| 4 | 1 | 0.05 | 0 |
| 5 | 2.5 | 0 | 0 |
| 6 | 2.5 | 0.01 | 0 |
| 7 | 2.5 | 0.05 | 0 |
| 8 | 2.5 | 0 | 0.002 |
| 9 | 2.5 | 0 | 0.010 |

All formulations gradually sedimented.

Examples 5 to 9 were examined for particle size over a one month period of storage in a 4° C./40° C. temperature cycling chamber.

Example 5 started with a larger particle size than Examples 6 to 9, indicating poorer dispersion. However, there was no significant change in particle size on storage. Examples 6 to 9 all showed a slight increase in particle size on storage, but not sufficient to equal the particle size of Example 5.

EXAMPLES 10 and 11

The following formulations were prepared in which the amounts are expressed in % w/w:

| Example | 10 | 11 |
|---|---|---|
| Budesonide | 0.280 | 0.653 |
| HFA 227 | 99.720 | |
| HFA 134a | — | 99.347 |

The formulation of Example 10 exhibited small flocs almost immediately which gradually floated to the surface.

The formulations of Example 11 exhibited small flocs almost immediately which gradually sank.

EXAMPLES 12 to 22

The formulations reported in the following Tables were prepared in which the amounts are expressed in % w/w:

| Example | 12 | 13 | 14 | 15 | 16 |
|---|---|---|---|---|---|
| Budesonide | 0.316 | 0.316 | 0.318 | 0.660 | 0.660 |
| Oleic Acid | 0.005 | 0.005 | 0.005 | 0.010 | 0.005 |
| Ethanol | 1.000 | 3.000 | 5.000 | 1.000 | 1.000 |
| HFA 227 | 29.902 | 29.296 | 28.690 | — | — |
| HFA 134a | 68.777 | 67.383 | 65.987 | 98.330 | 98.335 |

| Example | 17 | 18 | 19 | 20 | 21 | 22 |
|---|---|---|---|---|---|---|
| Budesonide | 0.632 | 0.632 | 0.632 | 0.329 | 0.316 | 0.316 |
| Oleic Acid | — | — | 0.005 | 0.005 | — | 0.001 |
| Ethanol | — | 0.994 | 1.000 | 1.000 | 1.000 | 1.000 |
| HFA 227 | 25.836 | 29.810 | 29.807 | — | 29.605 | 29.605 |
| HFA 134a | 73.532 | 68.564 | 68.556 | 98.666 | 69.079 | 69.078 |

The budesonide particles in the Formulations of 15, 16 and 20 sedimented.

The presence of ethanol and surfactant in the formulations improves the quality of the suspension.

Examples 12, 13 and 14 are density matched formulations employing different amounts of ethanol. Example 12 provided a stable formulation whereas the formulations of Examples 13 and 14 exhibited signs of degradation of the budesonide and crystal growth after prolonged storage.

Examples 17, 18, 19, 21 and 22 are density matched formulations. Example 22 exhibited less drug deposition than Example 21.

EXAMPLES 23 to 27

The formulations reported in the following Table were prepared in which the amounts are expressed in % w/w.

| Example | 23 | 24 | 25 | 26 | 27 |
|---|---|---|---|---|---|
| Budesonide | 0.079 | 0.079 | 0.079 | 0.079 | 0.158 |
| Oleic Acid | — | 0.001 | 0.004 | 0.008 | 0.001 |
| Ethanol | 1.000 | 1.000 | 1.000 | 1.000 | 1.000 |
| HFA 227 | 29.676 | 29.676 | 29.675 | 29.674 | 29.652 |
| HFA 134a | 69.245 | 69.244 | 69.242 | 69.239 | 69.189 |

Examples 23 to 27 are density matched formulations. In the density matched formulations the floc matrix remains more evenly dispersed in the formulation than in the formulations containing HFA 134a and HFA 227 as the only propellant. Examples 24 and 25 exhibited less drug deposition than Examples 23 and 26.

EXAMPLES 28 to 31

The formulations reported in the following Table were prepared in which the amounts are expressed in w/w.

| Example | 28 | 29 | 30 | 31 |
|---|---|---|---|---|
| Budesonide | 0.328 | 0.323 | 0.321 | 0.318 |
| Oleic Acid | 0.001 | 0.001 | 0.001 | 0.001 |
| Ethanol | 1.000 | 1.000 | 1.000 | 1.000 |
| HFA 227 | — | 9.868 | 14.802 | 19.736 |
| HFA 134a | 98.671 | 88.808 | 83.877 | 78.945 |

The formulations were compared, to Example 22. Example 22 was found to provide the slowest sedimentation rate. Decreasing levels of HFA 227 resulted in more rapid sedimentation rates.

EXAMPLES 32 to 36

The formulations reported in the following Table were prepared in which all parts are by weight.

| Example | 32 | 33 | 34 |
|---|---|---|---|
| Budesonide | 0.281 | 0.280 | 0.280 |
| Ethanol | 2.500 | 1.000 | 2.500 |
| Oleic Acid | — | 0.050 | 0.050 |
| HFA 227 | 97.219 | 98.670 | 97.170 |
| HFA 134a | — | — | — |

-continued

| Example | 35 | 36 |
|---|---|---|
| Budesonide | 0.280 | 0.280 |
| Ethanol | 2.500 | 2.500 |
| Span 85 | 0.002 | 0.010 |
| HFA 227 | 97.218 | 97.210 |

The formulations of Examples 32 to 36 creamed.

We claim:

1. A pharmaceutical aerosol formulation suitable for administration to a patient by oral or nasal inhalation consisting of a suspension of particulate budesonide, a hydrofluoroalkane propellant and optionally one or more of:
   (i) one or more additional hydrofluoroalkane propellants
   (ii) surfactant selected from oleic acid, sorbitan oleates and lecithin, and
   (iii) adjuvant having a Kauri-butanol value of at least 10.

2. A pharmaceutical aerosol formulation suitable for administration to a patient by oral or nasal inhalation consisting essentially of a suspension of budesonide particles in a mixture of hydrofluoroalkane propellants and optionally one or more excipients selected from:
   (i) an adjuvant having a Kauri-butanol value of at least 10,
   (ii) the combination of an adjuvant (i) and a surfactant selected from oleic acid, sorbitan oleates and lecithin,
   and
such that the liquid mixture has a density at 20° C. substantially equal to the density of budesonide.

3. A pharmaceutical aerosol formulation as claimed in claim 1 containing HFA 134a as a hydrofluoroalkane propellant.

4. A pharmaceutical aerosol formulation as claimed in claim 1 containing HFA 227 as a hydrofluoroalkane propellant.

5. A pharmaceutical aerosol formulation as claimed in claim 1 containing a propellant mixture of 15 to 35% by weight HFA 227 and from 65 to 85% by weight HFA 134a.

6. A pharmaceutical aerosol formulation as claimed in claim 1 in which the budesonide is present in an amount of 1 to 8 mg/ml of formulation.

7. A pharmaceutical aerosol formulation as claimed in claim 1 containing from 0.0001 to 1% by weight of surfactant.

8. A pharmaceutical aerosol formulation as claimed in claim 1 containing from 0.0005 to 0.01% by weight of surfactant.

9. A pharmaceutical aerosol formulation as claimed in claim 8 in which the surfactant is oleic acid.

10. A pharmaceutical aerosol formulation as claimed in claim 1 containing from about 0.5% to 3.5% by weight of an adjuvant having a Kauri-butanol value of at least 10.

11. A pharmaceutical aerosol formulation as claimed in claim 10 containing from about 1 to 2% by weight of an adjuvant having a Kauri-butanol value of at least 10.

12. A pharmaceutical aerosol formulation as claimed in claim 10 in which the adjuvant is ethanol.

13. A pharmaceutical aerosol formulation as claimed in claim 12 comprising about 1% by weight of ethanol.

14. A pharmaceutical aerosol formulation suitable for administration to a patient by oral or nasal inhalation consisting of:
   particulate budesonide,
   oleic acid, ethanol,
HFA 134a, and
HFA 227.

15. A pharmaceutical aerosol formulation suitable for administration to a patient by oral or nasal inhalation consisting of:

particulate budesonide,
oleic acid,
ethanol, and
HFA 134a.

* * * * *

UNITED STATES PATENT AND TRADEMARK OFFICE
CERTIFICATE OF CORRECTION

PATENT NO. : 6,039,932  
DATED : March 21, 2000  
INVENTOR(S) : Nayna Govind, Philip A. Jinks, Danna L. Ross, and Gary H. Ward Page 1 of 1

It is certified that error appears in the above-identified patent and that said Letters Patent is hereby corrected as shown below:

Column 6,  
Line 13, after the word "aerosol" please insert -- suspension --.  
Line 23, please delete the word "essentially".  
Line 62, after the word "aerosol" please insert -- suspension --.  
Line 65, after the word "particulate" please insert -- suspension of --.

Column 7,  
Line 4, after the word "aerosol" please insert -- suspension --.

Column 8,  
Line 1, after the word "particulate" please insert -- suspension of --.

Signed and Sealed this

Second Day of October, 2001

Attest:

NICHOLAS P. GODICI  
*Attesting Officer*     *Acting Director of the United States Patent and Trademark Office*